US00PP35375P2

(12) United States Plant Patent
Danziger

(10) Patent No.: US PP35,375 P2
(45) Date of Patent: Sep. 5, 2023

(54) ***SALVIA* PLANT NAMED 'DSALSYFBN'**

(50) Latin Name: *Salvia farinacea*
Varietal Denomination: DSALSYFBN

(71) Applicant: Danziger 'DAN' Flower Farm, Beit Dagan (IL)

(72) Inventor: Gavriel Danziger, Beit Dagan (IL)

(73) Assignee: Danziger "DAN" Flower Farm (IL)

( * ) Notice: Subject to any disclaimer, the term of this patent is extended or adjusted under 35 U.S.C. 154(b) by 0 days.

(21) Appl. No.: 18/075,259

(22) Filed: Dec. 5, 2022

(51) Int. Cl.
*A01H 5/02* (2018.01)
*A01H 6/50* (2018.01)

(52) U.S. Cl.
USPC ..... Plt./475

(58) Field of Classification Search
USPC ..... Plt./263.1, 475
See application file for complete search history.

(56) References Cited

U.S. PATENT DOCUMENTS

PP28,121 P3 * 6/2017 Danziger ..... A01H 5/12
Plt./475

* cited by examiner

*Primary Examiner* — Karen M Redden
(74) *Attorney, Agent, or Firm* — Cassandra Bright

(57) ABSTRACT

A new and distinct cultivar of *Salvia* plant named 'DSALSYFBN' is disclosed, characterized by abundant flowering, deep violet-blue flowers with violet sepals. Upright plants, flowering from early spring to late autumn. The new variety is a *Salvia*, normally produced as an outdoor garden or container plant.

2 Drawing Sheets

Figure 1:
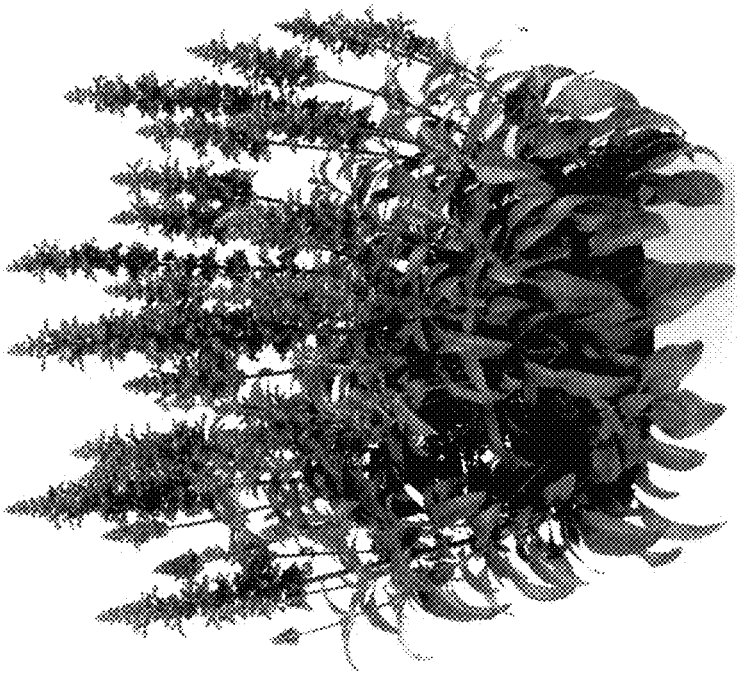

Latin name of the genus and species: *Salvia farinacea*.
Variety denomination: 'DSALSYFBN'.

BACKGROUND OF THE INVENTION

The new *Salvia* cultivar is the product of a planned breeding program conducted by the inventor, Gavriel Danziger, in Moshav Mishmar Hashiva, Israel. The objective of the breeding program was to produce new *Salvia* varieties for ornamental commercial applications. The crossing resulting in this new variety was made in 2014.

The seed parent is the unpatented, unnamed proprietary *Salvia farinacea* 'SAF-9-971'. The pollen parent is unknown as it was an open-pollination breeding program. The new variety was discovered in June 2015 by the inventor in a group of seedlings resulting from the 2014 open-pollination, in a research greenhouse in Moshav Mishmar Hashiva, Israel.

Asexual reproduction of the new cultivar was performed by vegetative cuttings. This was first performed at a research greenhouse in Moshav Mishmar Hashiva, Israel in July 2015, and has shown that the unique features of this cultivar are stable and reproduced true to type in multiple successive generations.

SUMMARY OF THE INVENTION

The cultivar 'DSALSYFBN' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DSALSYFBN' These characteristics in combination distinguish 'DSALSYFBN' as a new and distinct *Salvia* cultivar:

1. Short inflorescence internodes.
2. Abundant flowering stems.

PARENTAL COMPARISON

Plants of the new cultivar 'DSALSYFBN' are similar to plants of the seed parent, in most horticultural characteristics, however, plants of the new cultivar 'DSALSYFBN' differ in the following:

1. Flower color of the new variety is violet-blue, while the flower color of the seed parent is white.
2. Peduncles of the new variety are shorter than peduncles of the seed parent.

COMMERCIAL COMPARISONS

Plants of the new cultivar 'DSALSYFBN' are comparable to the commercial variety *Salvia* 'Sallyfun Blue Emotion', unpatented. The two *Salvia* varieties are similar in most horticultural characteristics; however, the new variety 'DSALSYFBN' differs in the following:

1. Plants of the new variety are more compact than plants of this comparator.
2. The new variety produces more flower stems than this comparator.

Plants of the new cultivar 'DSALSYFBN' can also be comparable to the unpatented commercial variety *Salvia* 'Sallyfun Blue Ice'. The two *Salvia* varieties are similar in most horticultural characteristics; however, the new variety 'DSALSYFBN' differs in the following:

1. Flower stems of the new variety are dark blue, while the flower stems of this comparator are white.

Plants of the new cultivar 'DSALSYFBN' can also be comparable to the commercial variety *Salvia* 'DSALDPOCN', U.S. Plant Pat. No. 28,121. The two *Salvia* varieties are similar in most horticultural characteristics; however, the new variety 'DSALSYFBN' differs in the following:

1. Foliage of the new variety is smaller than foliage of this comparator.
2. Main lip color of the new variety is Violet N89B; main lip color of this comparator is Violet-Blue 93C.
3. Sepal color of the new variety is Violet N89B; sepal color of this comparator is Violet-Blue 93A.

BRIEF DESCRIPTION OF THE PHOTOGRAPHS

The accompanying photograph in FIG. 1 illustrates in full color a typical plant of 'DSALSYFBN' grown in 25 cm pot outdoors in Moshav Mishmar Hashiva, Israel. Age of the plant photographed is approximately 4 months from a rooted cutting.

Figure 2:
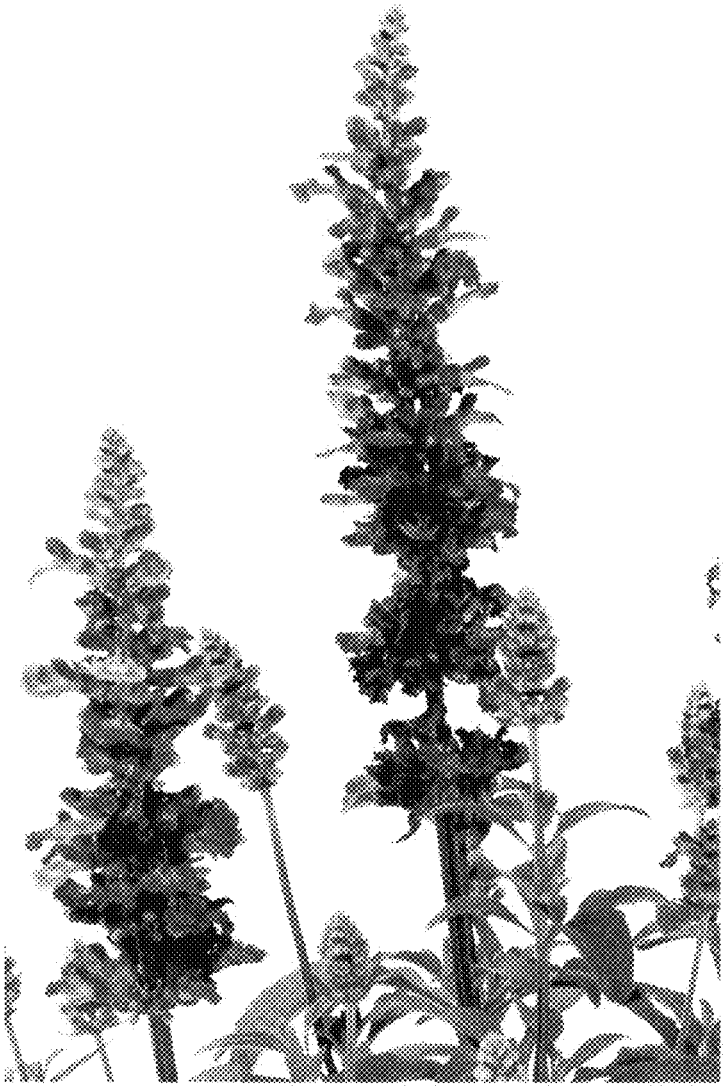

FIG. 2 illustrates a close-up view of typical inflorescences.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005, except where general terms of ordinary dictionary significance are used. The following observations and measurements describe 'DSALSYFBN' plants grown from autumn to spring in moderate climate in a greenhouse, in Moshav Mishmar Hashiva, Israel. General light conditions are bright, normal sunlight. Measurements and numerical values represent averages of typical plant types.

Botanical classification: *Salvia farinacea* 'DSALSYFBN'.

PROPAGATION

Type of propagation typically used: Vegetative cuttings.
Time to initiate roots: 5 to 7 days at approximately 25° C.
Time to produce a rooted cutting: 10 to 14 days at 25° C.
Root description: Moderately dense and fibrous. Medium brown in color, not accurately measured with RHS chart.

PLANT

Overall plant shape or growth habit: Upright.
Plant spread: 16 cm.
Plant height: 27 cm.
Growth rate: Rapid.
Length of primary lateral branches: Approximately 27 cm.
Diameter of lateral branches: Approximately 0.4 cm.
Quantity of lateral branches: About 4.
- *Color.*—Top Near RHS Yellow-Green 144A; bottom near Purple N92D.
- *Texture/pubescence.*—Puburulent, slightly ribbed longwise.

Internode length: Approximately 1 cm.
Age of plant described: Approximately 8 weeks from a rooted cutting.

FOLIAGE

Leaf:
- *Arrangement.*—Opposite.
- *Quantity.*—Approximately 20 per main branch.
- *Length.*—Approximately 4 cm.
- *Width.*—Approximately 2.5 cm.
- *Shape of blade.*—Ovate.
- *Apex.*—Apiculate.
- *Base.*—Obtuse.
- *Attachment.*—Petiolate.
- *Margin.*—Crenulate.
- *Texture of top surface.*—Lustrous.
- *Texture of bottom surface.*—Lustrous.
- *Color.*—Young foliage upper side: Near RHS Yellow-Green 147A. Young foliage under side: Near RHS Yellow-Green 146B. Mature foliage upper side: Near RHS Yellow-Green 147B. Mature foliage under side: Near RHS Yellow-Green 146B.
- *Venation.*—Type: Pinnate. Venation Color, Upper Side: Near RHS Yellow-Green 147B. Venation Color, Under Side: Near RHS Yellow-Green 147D.
- *Petiole.*—Length: Approximately 1 cm. Diameter: Approximately 0.1 cm. Color: Near RHS Yellow-Green 144A.

FLOWER

Natural flowering season: Early spring to late autumn in moderate climate.
Inflorescence type and habit: Spike.
Individual flower longevity on plant: About 3 to 5 days, depending on temperature.
Quantity of flowers: About 4 blooming spikes per plant.
Inflorescence size:
- *Diameter.*—Approximately 4 cm.
- *Height.*—Approximately 11 cm.
- *Flowers and buds per inflorescence.*—Approximately 46.
- *Inflorescence internodes.*—Average range 3 to 4 mm.

Peduncle:
- *Length.*—0.3 cm.
- *Diameter.*—0.1 cm.
- *Texture.*—Sericeous.
- *Color.*—Near RHS Violet-Blue N92B.
- *Orientation.*—About 30° from vertical.
- *Strength.*—Strong.

Individual flowers:
- *Diameter.*—Approximately 1 cm.
- *Length.*—Approximately 2 cm.
- *Persistence.*—Non-persistent.
- *Fragrance.*—Delicate.

Petals:
- *Petal arrangement.*—The corolla is sympetalous and typically bilabiate with 2 small, highly fused lobes forming an upper lip and 3 larger highly fused lobes forming a lower lip.
- *Margin.*—Slightly wavy.
- *Tip shape.*—Upper Lip: Rounded. Lower Lip: Blunt.
- *Length.*—Upper Lip: 0.5 cm. Lower Lip: 1 cm. Tube: 0.5 cm.
- *Width.*—Upper Lip: 0.3 cm. Lower Lip: 1 cm. Tube: 0.3 cm.

*Texture.*—Upper Lip: Villous. Lower Lip: Glabrous. Tube: Villous.

*Color.*—Upper Lip: When Opening: Inner Surface: Near RHS Violet N88B. Outer Surface: Near RHS Violet N89B. Fully Opened: Inner Surface: Near RHS Violet N88B. Outer Surface: Near RHS Violet N89B. Aging: Inner Surface: Near RHS Violet N88B. Outer Surface: Near RHS Violet N89B. Lower Lip: When Opening: Inner Surface: Near RHS Violet N89B and Violet-Blue 91D. Outer Surface: Near RHS Violet N89B and Violet-Blue 91D. Fully Opened: Inner Surface: Near RHS Violet N89B and Violet-Blue 91D. Outer Surface: Near RHS Violet N89C and Violet-Blue 91D. Aging: Inner Surface: Near RHS Violet N89B and Violet-Blue 91D. Outer Surface: Near RHS Violet N89C and Violet-Blue 91D. Tube: When Opening: Inner Surface: Near RHS Violet-Blue 92C. Outer Surface: Near RHS Violet-Blue 92A. Fully Opened: Inner Surface: Near RHS Violet-Blue 92C. Outer Surface: Near RHS Violet-Blue 92A. Aging: Inner Surface: Near RHS Violet-Blue 92C. Outer Surface: Near RHS Violet-Blue 92A.

Bud:

*Shape.*—Ovoid.

*Length.*—0.5 cm.

*Diameter.*—0.2 cm.

*Color.*—Near RHS Violet-Blue 93A.

Sepals:

*Quantity.*—2 lobes fused at base to form a tube.

*Length.*—Approximately 0.6 cm.

*Width.*—Approximately 0.3 cm.

*Margin.*—Flat.

*Texture.*—Velvety with rough lines longwise, pulverulent.

*Color.*—RHS Violet N89B.

Inflorescence bracts:

*Shape.*—Deltate.

*Length.*—8 mm.

*Diameter.*—2 to 3 mm.

*Color.*—Upper surface near Violet 86A, lower surface near Violet 86B.

*Persistence.*—Self-cleaning.

REPRODUCTIVE ORGANS

Stamens:

*Number.*—2.

*Filament length.*—Approximately 0.7 cm.

Anthers:

*Shape.*—Obovate.

*Length.*—Approximately 0.1 cm.

*Color.*—RHS Violet N89A.

*Pollen.*—Moderate quantity, colored near Violet N89A.

Pistil:

Number.—1.

*Length.*—Approximately 1.2 cm.

*Style.*—Length: Approximately 1 cm. Color: Near RHS Purple 85D.

*Stigma.*—Shape: V-shaped, one side longer than the other. Color: Near RHS Purple 85B. Ovary Color: Near RHS Yellow 1D.

OTHER CHARACTERISTICS

Seeds and fruits: Not observed.

Disease/pest resistance: Neither resistance nor susceptibility to normal diseases and pests of *Salvia* has been observed.

Temperature tolerance: USDA Zones 7 to 10.

Drought tolerance: Not observed tolerant to drought.

What is claimed is:

1. A new and distinct cultivar of *Salvia* plant named 'DSALSYFBN' as herein illustrated and described.

* * * * *